(12) United States Patent
Nöcker et al.

(10) Patent No.: US 12,383,478 B2
(45) Date of Patent: *Aug. 12, 2025

(54) COSMETIC PRODUCT FOR DYEING KERATIN FIBERS

(71) Applicant: KAO CORPORATION, Tokyo (JP)

(72) Inventors: Bernd Nöcker, Darmstadt (DE); Ines Rabelo De Moraes, Darmstadt (DE); Peter Bauer, Darmstadt (DE); Steven Breakspear, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/554,676

(22) PCT Filed: Apr. 26, 2022

(86) PCT No.: PCT/EP2022/061030
§ 371 (c)(1),
(2) Date: Oct. 10, 2023

(87) PCT Pub. No.: WO2022/229171
PCT Pub. Date: Nov. 3, 2022

(65) Prior Publication Data
US 2024/0197587 A1    Jun. 20, 2024

(30) Foreign Application Priority Data

Apr. 26, 2021 (EP) ..................... 21170394

(51) Int. Cl.
| | |
|---|---|
| *A61Q 5/10* | (2006.01) |
| *A61K 8/19* | (2006.01) |
| *A61K 8/22* | (2006.01) |
| *A61K 8/23* | (2006.01) |
| *A61K 8/34* | (2006.01) |
| *A61K 8/368* | (2006.01) |
| *A61K 8/46* | (2006.01) |
| *A61K 8/49* | (2006.01) |
| *A61Q 5/06* | (2006.01) |
| *A61Q 5/08* | (2006.01) |

(52) U.S. Cl.
CPC .......... *A61K 8/23* (2013.01); *A61K 8/19* (2013.01); *A61K 8/22* (2013.01); *A61K 8/347* (2013.01); *A61K 8/368* (2013.01); *A61K 8/466* (2013.01); *A61K 8/4946* (2013.01); *A61K 8/4953* (2013.01); *A61Q 5/065* (2013.01); *A61Q 5/08* (2013.01); *A61K 2800/4322* (2013.01); *A61K 2800/882* (2013.01)

(58) Field of Classification Search
CPC .......... A61K 8/4953; A61K 2800/4322; A61K 2800/88; A61K 8/41; A61K 2800/882; A61K 8/22; A61K 8/19; A61Q 5/065; A61Q 5/10
USPC ............................................ 8/405
See application file for complete search history.

(56) References Cited

U.S. PATENT DOCUMENTS

| | | | | |
|---|---|---|---|---|
| 4,668,236 | A  * | 5/1987  | Grollier ............... | A61K 8/418 8/405 |
| 4,931,066 | A  * | 6/1990  | Grollier ............... | A61K 8/418 8/408 |
| 10,052,273 | B2 * | 8/2018  | Lalleman ............. | A61K 8/498 |
| 10,485,744 | B2 * | 11/2019 | Wahler ................. | A61K 8/41 |
| 2010/0158844 | A1 | 6/2010 | Braida-Valerio et al. | |
| 2017/0258695 | A1* | 9/2017 | Consoli ................ | A61K 8/55 |
| 2017/0326048 | A1* | 11/2017 | Wahler ................. | A61K 8/19 |

FOREIGN PATENT DOCUMENTS

| | | |
|---|---|---|
| DE | 10 2007 041 493 A1 | 3/2009 |
| EP | 2 198 923 A2 | 6/2010 |
| WO | WO 2009/053180 A1 | 4/2009 |
| WO | WO 2021/084085 A1 | 5/2021 |

OTHER PUBLICATIONS

STIC Search Report dated Nov. 12, 2024.*
International Search Report & Written Opinion mailed on Jul. 18, 2022 in PCT/EP2022/061030 filed on Apr. 26, 2022 (9 pages).

(Continued)

*Primary Examiner* — Eisa B Elhilo
(74) *Attorney, Agent, or Firm* — Oblon, McClelland, Maier & Neustadt, L.L.P.

(57) ABSTRACT

A cosmetic product, containing a composition A including one or more alkalizing agents, an aqueous composition B having a pH in a range of 1 to 6 and containing one or more oxidizing agents, and a composition C containing one or more compounds selected from the following groups:

1)

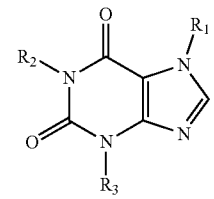

where $R_1$, $R_2$, and $R_3$ are independently selected from H and $CH_3$,
2) one or more orthodiphenols and salts thereof, and
3) one or more imidazolidin-2,4-diones and salts thereof.

20 Claims, No Drawings

(56) References Cited

OTHER PUBLICATIONS

European Search Report dated Nov. 4, 2021 in EP Application 21170394.7 filed on Aug. 6, 2019 (9 pages.
Database GNPD [Online] MINTEL; Jul. 2019, anonymous: "Caffeine Shampoo", Jul. 2019 Database accession No. 6713099, 2 pages.
Database GNPD [Online] MINTEL; Sep. 19, 2016 (Sep. 19, 2016), anonymous: "Permanent Hair Colour", XP055854644, Database accession No. 4282269, 4 pages.

\* cited by examiner

COSMETIC PRODUCT FOR DYEING KERATIN FIBERS

CROSS REFERENCE TO RELATED APPLICATIONS

This application is a National Stage entry under 35 U.S.C. § 371 of PCT/EP2022/061030, filed on Apr. 26, 2022, and claims priority to European Patent Application No. 21170394.7, filed on Apr. 26, 2021. The entire contents of both are incorporated herein by reference.

FIELD OF THE INVENTION

The present invention relates to cosmetic product for dyeing and/or bleaching of keratin fibers. Furthermore, methods for bleaching and/or dyeing are disclosed.

BACKGROUND OF THE INVENTION

Bleaching and dyeing processes were of particular interest of cosmetic industry over the past decades. Remaining challenges with these processes relate to damage, intensity, and durability.

Especially direct dyes have a low durability on keratin fibers, when keratin fibers experienced prior damage due to chemical services such as perming or bleaching. Chemical services alter the internal hair structure and usually allow for improved dye uptake in comparison to virgin hair, but simultaneously direct dyes are also easily washed out. Thus, consumers with prior chemical hair treatments may experience a low durability of the direct dyes, especially after several washes. Moreover, while the color intensity fades over several washes, the hair may experience an additional undesired color shift depending on the different bleeding rates of the individual direct dyes.

In everyday business operation of a hair dresser salon it is also not always easy for the professional to analyze prior hair damage of the customer, as some prior treatments may have already washed out and their effect is not visible anymore. While assuming healthy hair and then performing direct dyeing, it may come to a surprise to the hair dresser as well as the customer that durability of the dyeing treatment is exceptionally low. Such experiences will certainly frustrate every party.

In summary, the prior art has not satisfactorily solved the above challenges, and, therefore, there is a real need to develop direct dyeing compositions for keratin fibers, which deliver high dyeing intensity and have good durability, regardless of the history of chemical treatments.

The prior art has not sufficiently solved this problem.

For example, EP2198923 focuses on formulation stability, but not on chemical stability of aqueous oxidizing composition.

Xanthine and its derivatives are well-known ingredients in pharmaceutical and food industry. Moreover, cleansing compositions comprising caffeine are well-known (e.g. Mintel #6713099).

WO2009/053180 discloses aqueous oxidizing compositions comprising 5% by weight or less of hydrogen peroxide and purine derivatives, in particular caffeine. It was found that purine derivatives reduce damage to keratin fibers.

Despite the attempts of the prior art, there still is a need to improve the stability of hydrogen peroxide in combination with the dyeing performance of direct dyes.

SUMMARY OF THE INVENTION

The first object of the present invention is a cosmetic product for bleaching and/or dyeing of keratin fibers, preferably human keratin fibers, more preferably human hair, comprising:
a composition A comprising one or more alkalizing agent(s),
an aqueous composition B having a pH in the range of 1 to 6 and comprising one or more oxidizing agent(s), preferably hydrogen peroxide,
a composition C comprising one or more compound(s) selected from the following groups:
1)

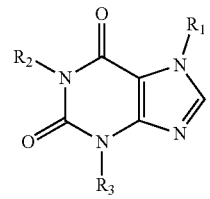

wherein $R_1$, $R_2$, and $R_3$ are independently selected from H and $CH_3$, and/or their mixtures,
2) one or more orthodiphenol(s) and/or their derivatives, and/or their mixtures, and/or their salt(s),
3) one or more imidazolidin-2,4-dione(s) and/or their derivatives, and/or their mixtures, and/or their salt(s).

The second object of the present invention is a method for dyeing of keratin fibers, preferably human keratin fibers, more preferably human hair, comprising the steps of:
i) providing compositions A, B, and C as defined above,
ii) mixing the compositions to yield a ready-to-use composition having a pH in the range of 7 to 12,
iii) applying the ready-to-use composition onto keratin fibers
iv) leaving it for a time period of 1 to 60 min and optionally heating the keratin fibers to a temperature range in the range of 40° C. to 60° C.
v) rinsing off the keratin fibers and optionally shampooing the keratin fibers.

The third object of the present invention is a method for bleaching and/or dyeing of keratin fibers, preferably human keratin fibers, more preferably human hair, comprising the steps of:
xi) providing compositions A, B, and C as defined above,
xii) mixing the compositions to yield a ready-to-use composition having a pH in the range of 7 to 12,
xiii) applying the ready-to-use composition onto keratin fibers
xiv) leaving it for a time period of 1 to 60 min and optionally heating the keratin fibers to a temperature range in the range of 40° C. to 60° C.
xv) rinsing off the keratin fibers and optionally shampooing the keratin fibers.

DETAILED DESCRIPTION OF THE INVENTION

Inventors of the present invention have unexpectedly found out that a cosmetic product according to claim 1 reduced the damage of bleaching compositions to keratin fibers, improved dyeing properties such as dyeing intensity and wash fastness of oxidative and direct dyes. Additionally, the three component product allowed for easy and accurate dosing of the active ingredients to the bleaching and/or dyeing mixture. Thus, the performance of the product was unexpectedly found to be increased.

Cosmetic Product

The present invention is directed to a cosmetic product for bleaching and/or dyeing of keratin fibers, preferably human keratin fibers, more preferably human hair, comprising:
  a composition A comprising one or more alkalizing agent (s),
  an aqueous composition B having a pH in the range of 1 to 6 and comprising one or more oxidizing agent(s), preferably hydrogen peroxide,
  a composition C comprising one or more compound(s) selected from the following groups:
  1)

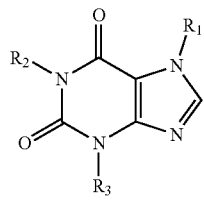

wherein $R_1$, $R_2$, and $R_3$ are independently selected from H and $CH_3$, and/or their mixtures,
  2) one or more orthodiphenol(s) and/or their derivatives, and/or their mixtures, and/or their salt(s),
  3) one or more imidazolidin-2,4-dione(s) and/or their derivatives, and/or their mixtures, and/or their salt(s).

Composition A

The present invention comprises a composition A comprising one or more alkalizing agent(s).

It is preferred from the viewpoint of providing alkalinity and cosmetic safety that one or more alkalizing agent(s) is/are one or more organic alkalizing agent(s) and/or ammonia and/or its salt(s).

Preferably, one or more organic alkalizing agent(s) are selected from alkyl and/or alkanolamine(s) and/or its/their salt(s), more preferably they/it is selected from monoethanolamine, diethanolamine, monoethanol methylamine, monoethanol dimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine, trimethylamine, triethylamine, 2-amino-2-methylpropanol, tris-(hydroxymethyl)-aminomethane and/or its/their salt(s), and/or their mixtures, from the viewpoint of providing alkalinity and cosmetic safety as well as their low odor.

The most preferred alkalizing agent(s) is selected from monoethanolamine, 2-amino-2-methylpropanol, tris-(hydroxymethyl)-aminomethane, and/or its/their salt(s), ammonia and or its salt(s), and/or their mixtures, from the viewpoint of providing alkalinity and cosmetic safety.

In one aspect of the present invention, it may be suitable from the viewpoint of storage stability that one or more alkalizing agent(s) is one or more inorganic alkalizing agent(s), preferably selected from metasilicates, carbonates, and/or bicarbonates, and/or their alkali or earth alkali salts, and/or their mixtures, preferably it is sodium metasilicate.

It is preferred from the viewpoint of providing alkalinity that the total concentration of alkalizing agent(s), preferably the total concentration of one or more alkanolamine(s) and/or its/their salt(s) and/or ammonia and/or its salt(s), is 0.1% by weight or more, more preferably 0.25% by weight or more, further more preferably 0.5% by weight or more, calculated to the total weight of the composition A.

It is preferred from the viewpoint of providing alkalinity, hair damage, and odor that the total concentration of alkalizing agent(s), preferably the total concentration of one or more alkanolamine(s) and/or its/their salt(s) and/or ammonia and/or its salt(s), is 40% by weight or less, more preferably 30% by weight or less, further more preferably 25% by weight or less, calculated to the total weight of the composition A.

For attaining the above-mentioned effects, it is preferred that the total concentration of alkalizing agent(s), preferably the total concentration of one or more alkanolamine(s) and/or its/their salt(s) and/or ammonia and/or its salt(s), is in the range of 0.1% to 40% by weight, preferably in the range of 0.25% to 30% by weight, more preferably in the range of 0.5% to 25% by weight, calculated to the total weight of the composition A.

Forms of Composition A

The composition A of the present invention may be available in various cosmetic forms such as liquid—aqueous or non-aqueous—composition or powder composition.

Powder Form of Composition A

In one aspect of the present invention, composition A may be a powder composition.

The term 'powder' denotes a solid composition at 25° C. and atmospheric pressure. The term relates to freely flowing powders as well as compressed powders such as tablets. The powder composition may also comprise water as long as its nature of the solid state at 25° C. is unchanged. Depending on the type of powder, a water content of 10% by weight or less, calculated to the total weight of the first composition A, may be acceptable. This does not exclude the presence of residual moisture from air or crystal water bound to ingredients. Preferably, the composition A is an anhydrous powder composition, from the viewpoint of stability.

It is further preferred that the composition A is a bleaching powder composition comprising one or more bleaching agent(s), preferably one or more persalt(s) and/or peroxy salt(s).

Suitable persalts and/or peroxy salts are sodium persulfate, potassium persulfate, ammonium persulfate, earth alkali peroxides such as magnesium peroxide, melamine peroxide or urea peroxide or phthalimidoperoxy hexanoic acid. The preferred persalts from the viewpoint of bleaching power are sodium, potassium and ammonium persulfate.

It is preferred from the viewpoint of bleaching power and cosmetic safety that the total concentration of persalts and/or peroxy salts in the bleaching powder composition A is in the range of 10% to 80% by weight, preferably in the range of 15% to 70% by weight, more preferably in the range of 20% to 60% by weight, and still more preferably in the range of 25% to 60% by weight, calculated to the total weight of the bleaching powder composition A.

It is preferred from the viewpoint of composition stability and convenience of use that the composition A comprises one or more pulverulent excipient.

The term 'excipient' denotes a compound, which may act as filling material and dispersant for the other compounds of the first composition A and do not react with the dyes and the alkalizing agent, and, thus, confer the powder a high degree of storage stability over an extended period of time.

The composition A of the present invention may comprise an organic and/or an inorganic pulverulent excipient in which the alkalizing agent and direct dyes are dispersed.

Suitable organic and/or an inorganic pulverulent excipients are, for example, diatomaceous earth, kaolin, bentonite, starch especially corn, tapioca, rice, wheat and potato, nylon powder, montmorillonit, gypsum, sawdust and perlite.

The total concentration of organic and/or an inorganic pulverulent excipient preferably is 50% by weight or more, more preferably 55% by weight or more, further more preferably 60% by weight or more, still further more preferably 65% by weight or more, even further more preferably 70% by weight or more, even more preferably 75% by weight or more, calculated to the total weight of the composition A, from the viewpoint of achieving good dispersability of the direct dyes in the powder and quick dissolution of the powder.

The total concentration of organic and/or an inorganic pulverulent excipient preferably is 98% by weight or less, more preferably 95% by weight or less, further more preferably 90% by weight or less, calculated to the total weight of the composition A, from the viewpoint of achieving good dispersability of the direct dyes in the powder and formulation freedom.

For attaining the above mentioned effects, the total concentration of organic and/or an inorganic pulverulent excipient preferably is in the range of 50% to 98% by weight, more preferably in the range of 55% to 95% by weight, further more preferably in the range of 60% to 90% by weight, still further more preferably 65% to 90% by weight, still further more preferably 70% to 90% by weight, even more preferably 75% to 90% by weight, calculated to the total weight of the composition A.

In another aspect of the present invention, it is preferred that composition A of the present invention is a dyeing powder composition.

In any case, composition A may comprise one or more direct dye(s).

In principle, all direct dyes are suitable for the purpose of the present inventions. In particular, anionic, cationic, or neutral direct dyes are suitable.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18, and HC Yellow 16.

Suitable cationic dyes are in principle those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic Red 51, Basic Yellow 87, HC Blue 17 and Basic Orange 31. The most preferred ones are Basic Red 51, Basic Yellow 87 Basic Orange 31, HC Blue 17 and Basic Blue 124.

Suitable neutral dyes including nitro dyes are HC Blue No.2, HC Blue No.4, HC Blue No.5, HC Blue No.6, HC Blue No.7, HC Blue No.8, HC Blue No.9, HC Blue No.10, HC Blue No.11, HC Blue No.12, HC Blue No.13, HC Brown No.1, HC Brown No.2, HC Green No.1, HC Orange No.1, HC Orange No.2, HC Orange No.3, HC Orange No.5, HC Red BN, HC Red No.1, HC Red No.3, HC Red No.7, HC Red No.8, HC Red No.9, HC Red No.10, HC Red No.11, HC Red No.13, HC Red No.54, HC Red No.14, HC Violet BS, HC Violet No.1, HC Violet No.2, HC Yellow No.2, HC Yellow No.4, HC Yellow No.5, HC Yellow No.6, HC Yellow No.7, HC Yellow No.8, HC Yellow No.9, HC Yellow No.10, HC Yellow No.11, HC Yellow No.12, HC Yellow No.13, HC Yellow No.14, HC Yellow No.15, 2-amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

It is preferred from the viewpoint of dyeing intensity and wash fastness, that one or more direct dye(s) is selected from HC Blue 18, HC Red 18, HC Yellow 16, Disperse Black 9, Acid Yellow 1, 2-amino-6-chloro-4-nitrophenol, and/or their salt(s), and/or their mixtures.

It is preferred from the viewpoint of color intensity that the total concentration of direct dyes is 0.001% by weight or more, further preferably 0.005% by weight or more, still more preferably 0.01% by weight or more, calculated to the total weight of the composition A.

It is preferred from the viewpoint of color intensity and economic reasons that the total concentration of direct dyes is 10% by weight or less, further preferably 5% by weight or less, still more preferably 3% by weight or less, still further more preferably 2% by weight or less, still further more preferably 1.5% by weight or less, calculated to the total weight of the composition A.

For attaining the above-mentioned effects, it is preferred that the total concentration of direct dyes is in the range of 0.001% to 10% by weight, preferably in the range of 0.005% to 5% by weight, more preferably in the range of 0.01% to 3% by weight, still further more preferably in the range of 0.01% to 2% by weight, still further more preferably in the range of 0.01% to 1.5% by weight, calculated to the total weight of the composition A.

Aqueous Composition

In one aspect of the present invention, composition A is an aqueous composition.

The term 'aqueous' denotes a composition that comprises a majority of water, i.e., composition A preferably comprises water at 50% by weight or more, further more preferably at 60% by weight or more, still more preferably at 70% by weight or more, still further more preferably at 80% by weight or more, calculated to the total weight of composition A, from the viewpoint of achieving a cosmetically acceptable composition.

It is further preferred from the viewpoint of dyeing intensity and/or lightening performance that the composition A comprises water at 98% by weight or less, more preferably at 95% by weight or less, further more preferably at 92% by weight or less, calculated to the total weight of composition A.

For achieving the above-mentioned effects, it is preferred that the total concentration of water in the composition A is in the range of 50% to 98% by weight, more preferably in the range of 60% to 95% by weight, further more preferably in the range of 70% to 92% by weight, still more preferably in the range of 80% to 92% by weight, calculated to the total weight of composition A.

It is preferred from the viewpoint of dyeing and/or lightening performance that the pH of the composition A is 8 or more, more preferably the pH is 8.5 or more, further more preferably the pH is 9 or more.

It is preferred from the viewpoint of hair damage and dyeing performance that the pH of the composition A is 12 or less, more preferably the pH is 11.5 or less, still more preferably the pH is 11 or less.

For attaining the above mentioned effects, it is preferred that the aqueous composition A has a pH in the range of 8 to 12, preferably in the range of 8.5 to 11, more preferably in the range of 9 to 11.

Preferably, composition A is a dyeing composition comprising one or more oxidative dye coupler(s) and/or oxidative dye precursor(s).

Suitable oxidative dye precursors are, for example, p-phenylendiamine and/or its derivatives, p-aminophenol and/or its derivatives, and heterocyclic compounds such as diaminopyrazols and substituted pyrimidines and/or their derivatives and/or their salts.

Furthermore, besides oxidative dye precursors, composition A may comprise oxidative dye couplers. Suitable oxidative dye couplers are, m-aminophenol and/or its derivatives, m-phenylenediamine and/or its derivatives, pyridines and/or its derivatives, and naphthol and/or its derivatives, and/or their salts.

The suitable total concentration of oxidative dye precursors and/or oxidative dye couplers and/or direct dyes is in the range of 0.001% to 5% by weight, preferably in the range of 0.01% to 4% by weight, more preferably in the range of 0.05% to 3% by weight, still more preferably in the range of 0.1% to 2% by weight, calculated to the total weight of the composition A.

It is preferred from the viewpoint of damage reduction and dyeing intensity that the oxidative dye precursors and/or oxidative dye couplers are different from the compound(s) according to group 2) of composition C.

Liquid Composition Comprising Less than 1% by Weight of Water

In another aspect of the present invention, composition A is a liquid composition at 25° C. and atmospheric pressure comprising one or more organic solvent(s) as compound(s) and less than 1% by weight of water, calculated to the total weight of the composition A. Preferably, the composition is anhydrous, from the viewpoint of dye stability.

The term 'liquid' denotes a physical state at 25° C. and atmospheric pressure, i.e., the dyeing composition is liquid at room temperature.

The term 'anhydrous' denotes a composition, which is free of added water. This does not exclude the presence of residual moisture from air or crystal water bound to ingredients.

It is preferred from the viewpoint of cosmetic application that composition A of the present aspect comprises one or more direct dye(s) as disclosed above.

For this aspect of the present invention, composition A may comprise one or more organic solvent(s).

The organic solvent(s) may be selected to dissolve the alkalizing agents and dyes. Preferred solvents are mono-, di-, and trivalent alcohols and/or their mixtures.

Preferred mono-, di-, and trivalent alcohols from the viewpoint of cosmetic safety and dissolution capacity are ethanol, n-propanol, isopropanol, propylene glycol, ethylene glycol, benzyl alcohol, phenoxyethanol, and glycerol, and/or their mixtures.

It is further preferred from the viewpoint of solution stability that the total concentration of organic solvents is 75% by weight or more, more preferably 80% by weight or more, further more preferably 85% by weight or more, calculated to the total weight of the composition A.

It is further preferred from the viewpoint of dyeing intensity that the total concentration of organic solvents is 98% by weight or less, more preferably 95% by weight or less, further more preferably 92% by weight or less, calculated to the total weight of composition A.

For attaining the above-mentioned effects, it is preferred that the total concentration of organic solvents is in the range of 75% to 98% by weight, more preferably 80% to 95% by weight, further more preferably in the range of 85% to 92% by weight, calculated to the total weight of composition A.

Aqueous Composition B

The aqueous composition B of the present invention has a pH in the range of 1 to 6 and comprises one or more oxidizing agent(s), preferably hydrogen peroxide.

It is preferred from the viewpoint of storage stability and safety of the composition that the pH of composition B is 1.25 or more, more preferably 1.5 or more, further more preferably 2 or more.

It is preferred from the viewpoint of storage stability of the composition that the pH of composition B is 5 or less, more preferably 4 or less, further more preferably 3 or less.

For attaining the above-mentioned effects, it is preferred that the pH of composition B is in the range of 1.25 to 5, more preferably in the range of 1.5 to 4, further more preferably in the range of 2 to 3.

It is further preferred from the viewpoint of product performance that the concentration of one or more oxidizing agent(s), preferably hydrogen peroxide, is 0.1% by weight or more, more preferably 0.25% by weight or more, further more preferably 1% by weight or more, calculated to the total weight of composition B.

It is further preferred from the viewpoint of product performance and user safety that the concentration of one or more oxidizing agent(s), preferably hydrogen peroxide, is 20% by weight or less, more preferably 15% by weight or less, further more preferably 12% by weight or less, calculated to the total weight of composition B.

For attaining the above-mentioned effects, it is preferred that the concentration of one or more oxidizing agent(s), preferably hydrogen peroxide, is in the range of more than 0.1% to 20% by weight, more preferably in the range of 0.25% to 15% by weight, further more preferably in the range of 1% to 12% by weight, calculated to the total weight of composition B.

Composition C

Composition C of the present invention comprises one or more compound(s) selected from the following as compound(s) according to group 1):

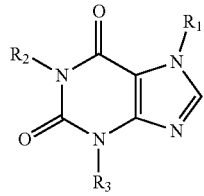

wherein $R_1$, $R_2$, and $R_3$ are independently selected from H and $CH_3$, and/or their mixtures. These compounds are xanthine and its derivatives.

Suitable xanthine and/or xanthine derivatives according to the structure of compound 1) are Xanthine with $R_1=R_2=R_3=H$,
Theobromine with $R_1=R_3=CH_3$ and $R_2=H$,
Theophylline with $R_2=R_3=CH_3$ and $R_1=H$, and
Caffeine with $R_1=R_2=R_3=CH_3$.

Mixtures of the above are suitable as well.

It is preferred from economic viewpoint that at least one or more compound(s) according to group 1) is/are caffeine and/or theobromine, and/or their mixtures, preferably it is caffeine.

It is preferred from the viewpoint of commercial availability that that one or more compound(s) according to group 2) of composition C is selected from
Flavonols,
Anthocyanidines,
Anthocyanines or anthocyanes,
Orthohydroxybenzoates,
Flavones,
Hydroxystilbenes,
3,4-dihydroxyphenylalanine and its derivatives,
2,3-dihydroxyphenylalanine and its derivatives,
4,5-dihydroxyphenylalanine and its derivatives,
Dihydroxycinnamates,
Orthopolyhydroxycoumarines,
Orhtopolyhydroxyisocoumarines,
Orthopolyhydroxycoumarones,
Orthopolyhydroxyisocoumarones,
Orhtopolyhydroxychalcones,
Orhtopolyhydroxychromones,
Orhtopolyhydroxyquinones,
Orhtohydroxyxanthones,
1,2-dihyroxybenzenes and its derivatives,
1,2,4-trihydroxybenzenes and its derivatives,
1,2,3-trihydroxybenzenes and its derivatives,
2,4,5-trihydroxybenzenes and its derivatives,
Proanthocyanidines,
Proanthocyanines,
Tannic acid,
Ellagic acid, one or more compound(s) according the following general structure:

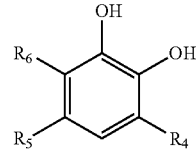

wherein $R_4$, $R_5$, and $R_6$ are independently selected from H, OH, halogen $C_1$-$C_{12}$ linear or branched alkyl or alkenyl, O—X, $NO_2$, COOH, $SO_3H$, aryl, heteroaryl, and/or their salt(s), and/or their mixtures, with X being $C_1$-$C_{12}$ linear or branched alkyl.

and/or their salt(s), and/or their mixture(s).

It is preferred from the viewpoint of commercial availability that one or more compound(s) according to group 2) of composition C is selected from the following general structure:

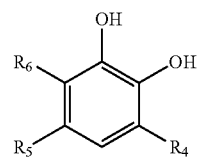

wherein $R_4$, $R_5$, and $R_6$ are independently selected from H, OH, halogen $C_1$-$C_{12}$ linear or branched alkyl or alkenyl, O—X, $NO_2$, COOH, $SO_3H$, aryl, heteroaryl, and/or their salt(s), and/or their mixtures, with X being $C_1$-$C_{12}$ linear or branched alkyl.

It is preferred from the viewpoint of dyeing intensity that for group 2) $R_4$ is selected from H, OH, halogen $C_1$-$C_{12}$ linear or branched alkyl or alkenyl, O—X, $NO_2$, COOH, $SO_3H$, aryl, heteroaryl, with X being $C_1$-$C_{12}$ linear or branched alkyl, and $R_5$, and $R_6$ are independently selected from $C_1$-$C_{12}$ linear or branched alkyl or alkenyl, O—X, $NO_2$, COOH, $SO_3H$, and/or their salt(s), and/or their mixtures, with X being $C_1$-$C_{12}$ linear or branched alkyl.

Preferably, at least one compound according to group 2) is selected from:

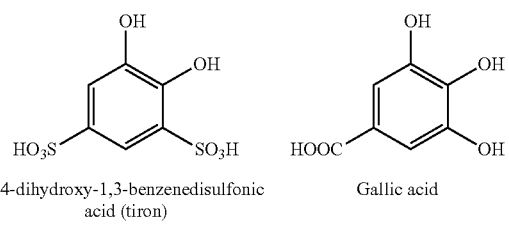

1,4-dihydroxy-1,3-benzenedisulfonic acid (tiron)          Gallic acid

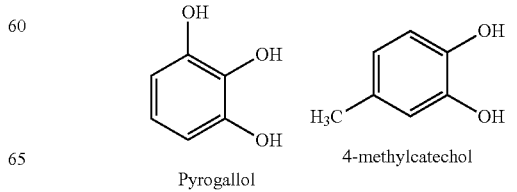

Pyrogallol          4-methylcatechol

-continued

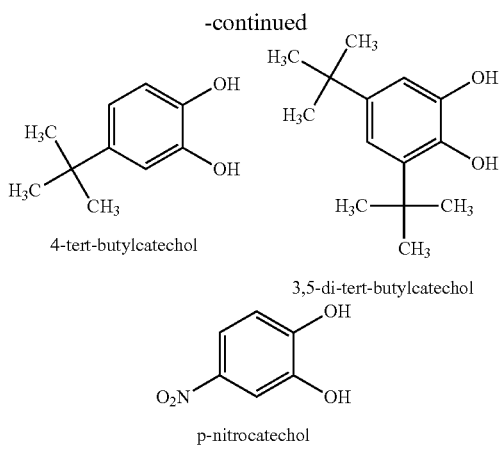

4-tert-butylcatechol 3,5-di-tert-butylcatechol

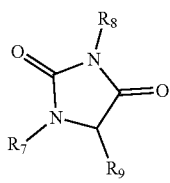

p-nitrocatechol and/or their salt(s), and/or their mixtures, more preferably one or more compound according to group 2) is tiron, gallic acid, and/or 4-methyl-catechol, and/or their salt(s), still more preferably one or more compound according to group 2) is tiron and/or its salt(s).

It is preferred from the viewpoint of commercial availability that one or more compound(s) according to group 3) of composition C is according to the following general structure:

$$\underset{R_7}{\overset{O}{\underset{N}{\bigvee}}}\underset{R_9}{\overset{R_8}{\underset{N}{\bigvee}}}O$$

wherein $R_7$, $R_8$, and $R_9$ are independently selected from H, OH, halogen, $C_1$-$C_{12}$ linear or branched alkyl or alkenyl, O—X, COOH, phenyl, diphenyl, ureyl, and/or their salt(s), and/or their mixtures, with X being $C_1$-$C_{12}$ linear or branched alkyl.

It is preferred from the viewpoint of commercial availability that one or more compound(s) according to group 3) of composition C is
  hydantoin,
  dichlordimethylhydantoin,
  bromchlordimethylhydantoin,
  dibromdimethylhydantoin,
  ethotoin,
  phenytoin,
  mephenytoin,
  fosphenytoin,
  allantoin,
and/or their salt(s), and/or their mixtures.

It is preferred from the viewpoint of commercial availability and dyeing intensity that one or more compound(s) according to group 3) of composition C is hydantoin or allantoin, and/or their salt(s), and/or their mixtures, preferably it is hydantoin and/or its salt(s).

It is further preferred from the viewpoint of stabilizing performance that the total concentration of compounds according to groups 1) to 3) is 0.001% by weight or more, more preferably 0.005% by weight or more, further more preferably 0.01% by weight or more, still more preferably 0.03% by weight or more, calculated to the total weight of composition C.

It is further preferred from the viewpoint of economic reasons as well as stabilizing performance that the total concentration of compounds according to groups 1) to 3) is 100% by weight or less, more preferably 90% by weight or less, further more preferably 80% by weight or less, still further more preferably 75% by weight or less, calculated to the total weight of composition C.

For attaining the above-mentioned effects, it is preferred from the viewpoint of stabilization and dyeing intensity that that the total concentration of compounds according to groups 1) to 3) is in the range of 0.001% to 100% by weight, preferably in the range of 0.005% to 90% by weight, more preferably in the range of 0.01% to 80% by weight, still more preferably in the range of 0.03% to 75% by weight, calculated to the total weight of composition C.

Forms of Composition C

Composition C of the present invention preferably may be a powder composition or a liquid composition. In case it is a liquid composition, it preferably is an aqueous emulsion, thickened gel, or a combination thereof, from the viewpoint of cosmetic safety as well as user friendliness. Independent of its form, it may comprise lipophilic compound(s) and/or surfactant(s).

It is preferred from the viewpoint of storage stability that composition C is a powder composition comprising one or more pulverulent excipient.

Preferably, the pulverulent excipient of composition C is selected from diatomaceous earth, kaolin, bentonite, starch especially corn, tapioca, rice, wheat and potato, nylon powder, montmorillonit, gypsum, sawdust and perlite.

It is preferred from the viewpoint of storage stability that the concentration of one or more pulverulent excipient in composition C is 10% by weight or more, more preferably 20% by weight or more, further more preferably 30% by weight or more, still more preferably 50% by weight or more, still more preferably 80% by weight or more, still more preferably 90% by weight or more, calculated to the total weight of the composition C.

In another aspect of the present invention, composition C is an aqueous composition.

For this aspect, it is preferred that the total concentration of water in composition C is 10% by weight or more, more preferably 20% by weight or more, further more preferably 30% by weight or more, still more preferably 50% by weight or more, still more preferably 80% by weight or more, still more preferably 90% by weight or more, calculated to the total weight of composition C.

In case composition C is an aqueous composition, the pH of the composition may be in the range of 3 to 12, preferably in the range of 5 to 11, more preferably in the range of 7 to 10.8.

Lipophilic Compounds

It is preferred from the viewpoint of user convenience that the compositions A, B, and/or C comprise(s) one or more lipophilic compound(s).

Preferably, lipophilic compounds are selected from $C_{12}$ to $C_{22}$ fatty alcohols, esters of $C_3$ to $C_{22}$ alcohols with $C_{12}$ to $C_{22}$ fatty acids, $C_8$ to $C_{22}$ fatty acids, vegetable oils, and/or silicones, and/or hydrocarbon-based products, and/or their mixtures, from the viewpoint of cosmetic compatibility.

Suitable $C_{12}$ to $C_{22}$ fatty alcohols are are myristyl alcohol, cetyl alcohol, stearyl alcohol, behenyl alcohol, and cetearyl alcohol.

Suitable esters of $C_3$ to $C_{22}$ alcohols with $C_{12}$ to $C_{22}$ fatty acids are isopropyl myristate, isopropyl palmitate, and myristyl myristate.

Suitable $C_8$ to $C_{22}$ fatty acids are oleic acid, linoleic acid, and palmitic acid.

Suitable vegetable oils are olive oil, almond oil, sunflower oil, and argan oil.

Suitable silicones are non-aminated and/or aminated silicones. The latter are commonly known as amodimethicones.

It is preferred from the viewpoint of forming a stable composition and user friendliness that the total concentration of lipophilic compounds is 1% by weight or more, more preferably 2% by weight or more, further more preferably 3% by weight or more, calculated to the total weight of each of the compositions A, B and/or C.

It is preferred from the viewpoint of forming a stable composition that the total concentration of lipophilic compounds is 20% by weight or less, more preferably 15% by weight or less, further more preferably 12% by weight or less, calculated to the total weight of each of the compositions A, B, and/or C.

For attaining the above-mentioned effects, the total concentration of lipophilic compounds is in the range of 1% to 20% by weight, preferably in the range of 2% to 15% by weight, more preferably in the range of 3% to 12% by weight, calculated to the total weight of each of the compositions A, B and/or C.

Surfactants

The compositions A, B, and/or C of the present invention may further comprise one or more surfactant(s), preferably selected from non-ionic surfactants, anionic surfactants, cationic surfactants, and/or amphoteric/zwitterionic surfactants, and/or their mixtures, more preferably selected from anionic surfactants, from the viewpoint of stabilizing the composition and improving wettability and mixability.

Preferably, the anionic surfactants may be selected from ethoxylated or non-ethoxylated alkyl ether sulfate surfactants, alkyl sulfates, ethoxylated and/or non-ethoxylated alkyl carboxylates, ethoxylated or non-ethoxylated amino acid surfactants, and/or their mixtures, and/or their salts.

Suitable examples are alkyl sulfate or preferably ethoxylated alkyl ether sulfate surfactants or mixtures thereof, and/or salts thereof, having an alkyl chain length of $C_{10}$ to $C_{22}$ and an ethoxylation degree from 1 to 50.

Suitable non-ionic surfactants may be selected from alkyl polyglycosides, ethoxylated triglycerides, ethoxylated fatty alcohols, ethoxylated fatty acid esters, and/or their mixtures.

Suitable cationic surfactants are quaternary ammonium surfactants having a carbon chain length in the range of $C_{12}$ to $C_{22}$ or surfactants having a tertiary amine group and at least one alkyl chain having a carbon chain length in the range of $C_{12}$ to $C_{22}$ such as alkylamidoalkylamine surfactants, and/or their salts. Suitable examples are cetrimonium chloride and behentrimonium chloride.

Suitable amphoteric/zwitterionic surfactants are of betaine type. Suitable compounds may be selected from alkyl betaines and/or alkylamido betaines. A preferred compound selected from alkyl betaines is lauryl betaine. A preferred compound selected from alkylamido betaines is cocamidopropyl betaine. The disclosure also relates to the salts of the compounds.

Suitable concentration ranges for surfactants are in the range of 0.1% to 10% by weight, calculated to the total weight of each of the compositions A, B, and/or C, from the viewpoint of enhancing wettability of keratin fibers, physical stability, and mixability with other compositions.

Thickening Polymers

From the viewpoint of cosmetic safety, it is further preferred that the compositions A, B, and/or C of the present invention may comprise one or more thickening polymer(s).

The compositions A, B, and/or C of the present invention may comprise(s) one or more thickening polymer(s) selected from non-ionic thickening polymers and/or anionic thickening polymers, and/or their mixtures.

Preferably, the thickening polymers are selected from polymers resulting in an aqueous solution and/or aqueous dispersion at pH between 1 and 6 having a viscosity of at least 1,000 mPa·s measured at a polymer concentration of 1% by weight in water at 25° C. under atmospheric conditions, calculated to the total weight of the composition, determined by a Brookfield viscometer, such as at 10 rpm for 1 min with spindle #4 at 25° C.

Suitable non-ionic thickening polymers are cellulose-based polymers. Suitable examples of cellulose-based polymers are methylcellulose, hydroxymethylcellulose, hydroxyethylcellulose, hydroxypropylcellulose, hydroxyethyl-methylcellulose, and alkylated hydroxyl celluloses such as $(C_2\text{-}C_8)$-alkylcelluloses or cetyl hydroxyethylcellulose.

Suitable anionic thickening polymers are selected from naturally-based anionic polymers and/or synthetic anionic polymers.

Suitably, the natural anionic polymer(s) may be selected from xanthan gum, dehydroxanthan gum, hydroxypropylxanthan gum, carboxymethyl cellulose and starch based polymers such as vegetable starch and/or their synthetically modified derivatives such as hydroxypropyl starch phosphate. Equally suitable are alginic acids, sodium alginates, ammonium alginates, calcium alginates, gum arabic, and guar gum.

Suitable synthetic anionic polymers are associative thickening polymers, such as acrylates/steareth-30 methacrylate copolymer.

The preferred thickening polymer for the composition of the present invention are natural anionic polymers, more preferably xanthan gum and/or dehydroxanthan gum, from the viewpoint of their biodegradability and low environmental impact.

Preferably, the total concentration of thickening polymers in the compositions A, B, and/or C of the present invention is/are 0.1% by weight or more, more preferably 0.25% by weight or more, more preferably 0.5% by weight or more, calculated to the total weight of each of the compositions A, B, and/or C, from the viewpoint of providing sufficient viscosity to compositions A, B and/or C.

Preferably, the total concentration of thickening polymers in the compositions A, B and/or C of the present invention is 15% by weight or less, more preferably 12% by weight or more, further more preferably 10% by weight or less, calculated to the total weight of each of the compositions A, B and/or C, from the viewpoint of providing sufficient viscosity to the compositions A, B and/or C and cost of goods.

For attaining the above-mentioned effects, it is preferred that the total concentration of thickening polymers in the compositions A, B and/or C of the present invention is in the range of 0.1% to 15% by weight, preferably in the range of 0.25% to 12% by weight, more preferably in the range of 0.5% to 10% by weight, calculated to the total weight of each of the compositions A, B and/or C.

It is preferred from the viewpoint of cosmetic safety that the compositions A, B and/or C of the present invention has/have a viscosity in the range of 1,000 Pas to 25,000 mPas, preferably 2,000 mPas to 20,000 mPas, more preferably in the range of 2,500 mPas to 17,500 mPas, determined by cone plate viscometry at 25° C. under atmospheric conditions. A suitable viscometer is a Brookfield viscometer with spindle #4.

Method for Dyeing

The present invention is also directed to a method for dyeing of keratin fibers, preferably human keratin fibers, more preferably human hair, comprising the steps of:
  i) providing compositions A, B, and C as defined above,
  ii) mixing the compositions to yield a ready-to-use composition having a pH in the range of 7 to 12,
  iii) applying the ready-to-use composition onto keratin fibers
  iv) leaving it for a time period of 1 to 60 min and optionally heating the keratin fibers to a temperature range in the range of 40° C. to 60° C.
  v) rinsing off the keratin fibers and optionally shampooing the keratin fibers.

Suitably, the pH of the ready-to-use composition is in the range of 7 to 12. It is preferred from the viewpoint of accelerated dyeing that the pH of the ready-to-use composition is in the range of 7.5 to 11, more preferably 8.0 to 10.5.

The ready-to-use composition is then applied to keratin fibers and left for a time period of 1 min to 60 min as defined in step iv). Preferred time ranges for step iv) are 5 min to 45 min, more preferred ranges are 10 min to 35 min, from the viewpoint of sufficiently bleaching/lightening.

Optionally, heat may be applied while leaving the ready-to-use composition onto keratin fibers. Suitable temperature ranges are 30° C. to 50° C.

Method for Bleaching

The present invention is also directed to method for bleaching and/or dyeing of keratin fibers, preferably human keratin fibers, more preferably human hair, comprising the steps of:
  xi) providing compositions A, B, and C as defined in any of the claims 1 to 13,
  xii) mixing the compositions to yield a ready-to-use composition having a pH in the range of 7 to 12,
  xiii) applying the ready-to-use composition onto keratin fibers
  xiv) leaving it for a time period of 1 to 60 min and optionally heating the keratin fibers to a temperature range in the range of 40° C. to 60° C.
  xv) rinsing off the keratin fibers and optionally shampooing the keratin fibers.

Suitably, the pH of the ready-to-use composition is in the range of 7 to 12. It is preferred from the viewpoint of accelerated dyeing that the pH of the ready-to-use composition is in the range of 7.5 to 11, more preferably 8.0 to 10.5.

The ready-to-use composition is then applied to keratin fibers and left for a time period of 1 min to 60 min as defined in step xiv). Preferred time ranges for step xiv) are 5 min to 45 min, more preferred ranges are 10 min to 35 min, from the viewpoint of sufficiently bleaching/lightening.

Optionally, heat may be applied while leaving the ready-to-use composition onto keratin fibers. Suitable temperature ranges are 30° C. to 50° C.

The present disclosure is also directed to <1> a cosmetic product for bleaching and/or dyeing of keratin fibers, preferably human keratin fibers, more preferably human hair, comprising:
  a composition A comprising one or more alkalizing agent(s),
  an aqueous composition B having a pH in the range of 1 to 6 and comprising one or more oxidizing agent(s), preferably hydrogen peroxide,
  a composition C comprising one or more compound(s) selected from the following groups:
  1)

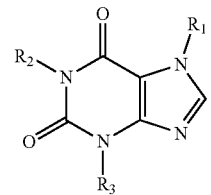

wherein $R_1$, $R_2$, and $R_3$ are independently selected from H and $CH_3$, and/or their mixtures,
  2) one or more orthodiphenol(s) and/or their derivatives, and/or their mixtures, and/or their salt(s),
  3) one or more imidazolidin-2,4-dione(s) and/or their derivatives, and/or their mixtures, and/or their salt(s).

<2> The product according to clause <1> characterized in that the one or more alkalizing agent(s) of composition A is/are one or more organic alkalizing agent(s), and/or ammonia, and/or its salt(s).

<3> The product according to any of the clauses <1> to <2> characterized in that one or more organic alkalizing agent(s) of composition A is/are selected from alkyl and/or alkanolamine(s) and/or its/their salt(s), more preferably they/it is selected from monoethanolamine, diethanolamine, monoethanol methylamine, monoethanol dimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine, trimethylamine, triethylamine, 2-amino-2-methylpropanol, tris-(hydroxymethyl)-aminomethane and/or its/their salt(s), and/or their mixtures.

<4> The product according to any of the clauses <1> to <3> characterized in that the one or more alkalizing agent(s) of composition A is selected from monoethanolamine, 2-amino-2-methylpropanol, tris-(hydroxymethyl)-aminomethane, and/or its/their salt(s), ammonia and or its salt(s), and/or their mixtures.

<5> The product according to clause <1> characterized in that the one or more alkalizing agent(s) of composition A is one or more inorganic alkalizing agent(s), preferably selected from metasilicates, carbonates, and/or bicarbonates, and/or their alkali or earth alkali salts, and/or their mixtures, more preferably it is sodium metasilicate.

<6> The product according to any of the clauses <1> to <5> characterized in that the total concentration of alkalizing agent(s), preferably the total concentration of one or more alkanolamine(s) and/or its/their salt(s) and/or ammonia and/or its salt(s), is in the range of 0.1% to 40% by weight, preferably in the range of 0.25% to 30% by weight, more preferably in the range of 0.5% to 25% by weight, calculated to the total weight of composition A.

<7> The product according to any of the clauses <1> to <6> characterized in that composition A is a powder composition.

<8> The product according to clause <7> characterized in that composition A comprises water at 10% by weight or less, calculated to the total weight of composition A, preferably it is anhydrous.

<9> The product according to any of the clauses <7> and/or <8> characterized in that composition A is a bleaching powder composition comprising one or more bleaching agent(s), preferably one or more persalt(s) and/or peroxy salt(s).

<10> The product according to clause <9> characterized in that the total concentration of one or more persalt(s) and/or peroxy salt(s) in composition A is in the range of 10% to 80% by weight, preferably in the range of 15% to 70% by weight, more preferably in the range of 20% to 60% by weight, and still more preferably in the range of 25% to 60% by weight, calculated to the total weight of the bleaching powder composition A.

<11> The product according to any of the clauses <1> to <8> characterized in that composition A is a dyeing powder composition.

<12> The product according to any of the clauses <1> to <11> characterized in that composition A comprises one or more pulverulent excipient(s).

<13> The product according to clause <12> characterized in that composition A comprises one or more organic and/or an inorganic pulverulent excipient.

<14> The product according to clause <13> characterized in that the organic and/or an inorganic pulverulent excipients is/are diatomaceous earth, kaolin, bentonite, starch especially corn, tapioca, rice, wheat and potato, nylon powder, montmorillonit, gypsum, sawdust and perlite.

<15> The product according to any of the clauses <12> to <14> characterized in that the total concentration of organic and/or an inorganic pulverulent excipient in composition A is in the range of 50% to 98% by weight, more preferably in the range of 55% to 95% by weight, further more preferably in the range of 60% to 90% by weight, still further more preferably 65% to 90% by weight, still further more preferably 70% to 90% by weight, even more preferably 75% to 90% by weight, calculated to the total weight of composition A.

<16> The product according to any of the clauses <1> to <6> characterized in that composition A is an aqueous composition having a pH in the range of 8 to 12, preferably in the range of 8.5 to 11.5, more preferably in the range of 9 to 11.

<17> The product according to any of the clauses <1> to <6> and/or <16> characterized in that composition A is a dyeing composition comprising one or more oxidative dye coupler(s) and/or oxidative dye precursor(s).

<18> The product according to any of the clauses <1> to <6> and/or <16> to <17> characterized in that composition A comprises oxidative dye precursors, preferably p-phenylendiamine and/or its derivatives, p-aminophenol and/or its derivatives, and heterocyclic compounds such as diaminopyrazols and substituted pyrimidines, and/or their derivatives, and/or their salts.

<19> The product according to any of the clauses <1> to <6> and/or <16> to <18> characterized in that composition A comprises oxidative dye couplers, preferably, m-aminophenol and/or its derivatives, m-phenylenediamine and/or its derivatives, pyridines and/or its derivatives, and naphthol and/or its derivatives, and/or their salts.

<20> The product according to any of the clauses <1> to <6> and/or <16> to <19> characterized in that the total concentration of oxidative dye precursors and/or oxidative dye couplers in composition A is in the range of 0.001% to 5% by weight, preferably in the range of 0.01% to 4% by weight, more preferably in the range of 0.05% to 3% by weight, still more preferably in the range of 0.1% to 2% by weight, calculated to the total weight of composition A.

<21> The product according to any of the clauses <11> to <20> characterized in that composition A comprises one or more pulverulent excipient.

<22> The product according to clause <21> characterized in that composition A comprises one or more organic and/or an inorganic pulverulent excipient.

<23> The product according to clause <22> characterized in that the organic and/or an inorganic pulverulent excipients is/are diatomaceous earth, kaolin, bentonite, starch especially corn, tapioca, rice, wheat and potato, nylon powder, montmorillonit, gypsum, sawdust and perlite.

<24> The product according to any of the clauses <21> to <23> characterized in that the total concentration of organic and/or an inorganic pulverulent excipient in composition A is in the range of 50% to 98% by weight, more preferably in the range of 55% to 95% by weight, further more preferably in the range of 60% to 90% by weight, still further more preferably 65% to 90% by weight, still further more preferably 70% to 90% by weight, even more preferably 75% to 90% by weight, calculated to the total weight of composition A.

<25> The product according to any of the clauses <1> to <24> characterized in that composition A comprises one or more direct dye(s), preferably one or more non-ionic, anionic, cationic, and/or amphoteric direct dye(s), more preferably one or more direct dye(s) selected from Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18, and HC Yellow 16, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic Red 51, Basic Yellow 87, HC Blue 17 and Basic Orange 31. The most preferred ones are Basic Red 51, Basic Yellow 87 Basic Orange 31, HC Blue 17 and Basic Blue 124, HC Blue No.2, HC Blue No.4, HC Blue No.5, HC Blue No.6, HC Blue No.7, HC Blue No.8, HC Blue No.9, HC Blue No.10, HC Blue No.11, HC Blue No.12, HC Blue No.13, HC Brown No.1, HC Brown No.2, HC Green No.1, HC Orange No.1, HC Orange No.2, HC Orange No.3, HC Orange No.5, HC Red BN, HC Red No.1, HC Red No.3, HC Red No.7, HC Red No.8, HC Red No.9, HC Red No.10, HC Red No.11, HC Red No.13, HC Red No.54, HC Red No.14, HC Violet BS, HC Violet No.1, HC Violet No.2, HC Yellow No.2, HC Yellow No.4, HC Yellow No.5, HC Yellow No.6, HC Yellow No.7, HC Yellow No.8, HC Yellow No.9, HC Yellow No.10, HC Yellow No.11, HC Yellow No.12, HC Yellow No.13, HC Yellow No.14, HC Yellow No.15, 2-amino-6-chloro-4-nitrophenol, tetrabromophenol blue, picramic acid, and 2-hydroxyethylpicramic acid, and/or their salt(s), and/or their mixtures.

<26> The product according to any of the clauses <1> to <25> characterized in that one or more direct dye(s) is selected from HC Blue 18, HC Red 18, HC Yellow 16, Disperse Black 9, Acid Yellow 1, 2-amino-6-chloro-4-nitrophenol, tetrabromophenol blue, and/or their salt(s), and/or their mixtures.

<27> The product according to any of the clauses <1> to <26> characterized in that the total concentration of direct dyes in composition A is in the range of 0.001% to 10% by weight, preferably in the range of 0.005% to 5% by weight, more preferably in the range of 0.01% to 3% by weight, still further more preferably in the range of 0.01% to 2% by weight, still further more preferably in the range of 0.01% to 1.5% by weight, calculated to the total weight of composition A.

<28> The product according to any of the clauses <1> to <6> and/or <25> to <27> characterized in that composition A is a liquid composition at 25° C. and atmospheric pressure comprising one or more organic solvent(s) as compound(s) and less than 1% by weight of water, calculated to the total weight of composition A.

<29> The product according to clause <28> characterized in that composition A is anhydrous.

<30> The product according to any of the clauses <28> to <29> characterized in that organic solvent(s) of composition A are mono-, di-, and trivalent alcohols and/or their mixtures.

<31> The product according to any of the clauses <28> to <30> characterized in that the organic solvent(s) of composition A is/are ethanol, n-propanol, isopropanol, propylene glycol, ethylene glycol, benzyl alcohol, phenoxyethanol, and glycerol, and/or their mixtures.

<32> The product according to any of the clauses <28> to <31> characterized in that the total concentration of organic solvents in composition A is in the range of 75% to 98% by weight, more preferably 80% to 95% by weight, further more preferably in the range of 85% to 92% by weight, calculated to the total weight of composition A.

<33> The product according to any of the clauses <1> to <32> characterized in that the pH of the composition B is in the range of 1.25 to 5, more preferably in the range of 1.5 to 4, further more preferably in the range of 2 to 3.

<34> The product according to any of the clauses <1> to <33> characterized in that the concentration of one or more oxidizing agent(s), preferably hydrogen peroxide, in composition B is in the range of more than 0.1% to 20% by weight, more preferably in the range of 0.25% to 15% by weight, further more preferably in the range of 1% to 12% by weight, calculated to the total weight of composition B.

<35> The product according to any of the clauses <1> to <34> characterized in that one or more compound(s) according to group 1) of composition C is/are xanthine and/or xanthine derivatives, preferably xanthine, theobromine, theophylline, caffeine, and/or their mixtures.

<36> The product according to any of the clauses <1> to <35> characterized in that one or more compound(s) according to group 1) of composition C is/are is/are caffeine and/or theobromine, and/or their mixtures, preferably it is caffeine.

<37> The product according to any of the clauses <1> to <36> characterized in that one or more compound(s) according to group 2) of composition C is selected from
Flavonols,
Anthocyanidines,
Anthocyanines or anthocyanes,
Orthohydroxybenzoates,
Flavones,
Hydroxystilbenes,
3,4-dihydroxyphenylalanine and its derivatives,
2,3-dihydroxyphenylalanine and its derivatives,
4,5-dihydroxyphenylalanine and its derivatives,
Dihydroxycinnamates,
Orthopolyhydroxycoumarines,
Orhtopolyhydroxyisocoumarines,
Orthopolyhydroxycoumarones,
Orthopolyhydroxyisocoumarones,
Orhtopolyhydroxychalcones,
Orhtopolyhydroxychromones,
Orhtopolyhydroxyquinones,
Orhtohydroxyxanthones,
1,2-dihyroxybenzenes and its derivatives,
1,2,4-trihydroxybenzenes and its derivatives,
1,2,3-trihydroxybenzenes and its derivatives,
2,4,5-trihydroxybenzenes and its derivatives,
Proanthocyanidines,
Proanthocyanines,
Tannic acid,
Ellagic acid,
one or more compound(s) according the following general structure:

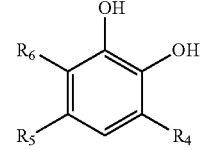

wherein $R_4$, $R_5$, and $R_6$ are independently selected from H, OH, halogen $C_1$-$C_{12}$ linear or branched alkyl or alkenyl, O—X, $NO_2$, COOH, $SO_3H$, aryl, heteroaryl, and/or their salt(s), and/or their mixtures, with X being $C_1$-$C_{12}$ linear or branched alkyl.
and/or their salt(s), and/or their mixture(s).

<38> The product according to any of the clauses <1> to <37> characterized in that for group 2) of composition C one or more compound(s) is according to the following general structure:

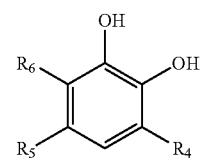

wherein $R_4$, $R_5$, and $R_6$ are independently selected from H, OH, halogen $C_1$-$C_{12}$ linear or branched alkyl or alkenyl, O—X, NO₂, COOH, SO₃H, aryl, heteroaryl, and/or their salt(s), and/or their mixtures, with X being $C_1$-$C_{12}$ linear or branched alkyl.

<39> The product according to any of the clauses <1> to <38> characterized in that for group 2) of composition B $R_4$ is selected from H, OH, halogen $C_1$-$C_{12}$ linear or branched alkyl or alkenyl, O—X, NO₂, COOH, SO₃H, aryl, heteroaryl, with X being $C_1$-$C_{12}$ linear or branched alkyl, and $R_5$, and $R_6$ are independently selected from $C_1$-$C_{12}$ linear or branched alkyl or alkenyl, O—X, NO₂, COOH, SO₃H, and/or their salt(s), and/or their mixtures, with X being $C_1$-$C_{12}$ linear or branched alkyl.

<40> The product according to any of the clauses <1> to <39> characterized in that at least one compound according to group 2) of composition C is selected from:

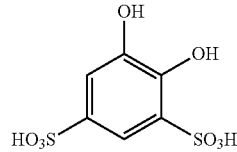
1,4-dihydroxy-1,3-benzenedisulfonic acid (tiron)

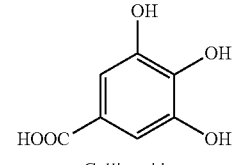
Gallic acid

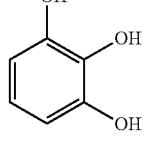
Pyrogallol

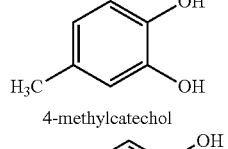
4-methylcatechol

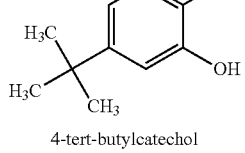
4-tert-butylcatechol

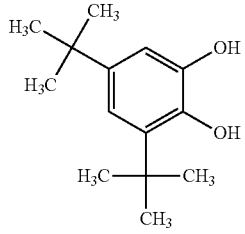
3,5-di-tert-butylcatechol

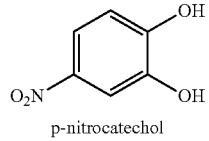
p-nitrocatechol and/or their salt(s), and/or their mixtures.

<41> The product according to any of the clauses <1> to <40> characterized in that one or more compound according to group 2) is tiron, gallic acid, and/or 4-methyl-catechol, and/or their salt(s), still more preferably one or more compound according to group 2) is tiron and/or its salt(s).

<42> The product according to any of the clauses <1> to <41> characterized in that the total concentration of compounds according to group 1) of composition C is in the range of 0.001% to 20% by weight, preferably in the range of 0.005% to 15% by weight, more preferably in the range of 0.01% to 12% by weight, still more preferably in the range of 0.03% to 10% by weight, calculated to the total weight of composition C.

<43> The product according to any of the clauses <1> to <42> characterized in that the total concentration of tiron and/or its salt(s) in composition C in the range of 0.001% to 20% by weight, preferably in the range of 0.005% to 15% by weight, more preferably in the range of 0.01% to 12% by weight, still more preferably in the range of 0.03% to 10% by weight, calculated to the total weight of composition C.

<44> The product according to any of the clauses <1> to <43> characterized in that one or more compound(s) according to group 3) of composition C is according to the following general structure:

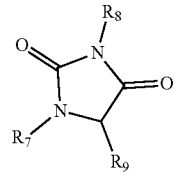

wherein $R_7$, $R_8$, and $R_9$ are independently selected from H, OH, halogen, $C_1$-$C_{12}$ linear or branched alkyl or alkenyl, O—X, COOH, phenyl, diphenyl, ureyl, and/or their salt(s), and/or their mixtures, with X being $C_1$-$C_{12}$ linear or branched alkyl.

<45> The product according to any of the clauses <1> to <44> characterized in that one or more compound(s) according to group 3) of composition C is:
  hydantoin,
  dichlordimethylhydantoin,
  bromchlordimethylhydantoin,
  dibromdimethylhydantoin,
  ethotoin,
  phenytoin,
  mephenytoin,
  fosphenytoin,
  allantoin,
and/or their salt(s), and/or their mixtures.

<46> The product according to any of the clauses <1> to <45> characterized in that one or more compound(s) according to group 3) of composition C is hydantoin or allantoin, and/or their salt(s), and/or their mixtures.

<47> The product according to any of the clauses <1> to <46> characterized in that one or more compound(s) according to group 3) of composition C is hydantoin and/or its salt(s).

<48> The product according to any of the clauses <1> to <47> characterized in that the total concentration of compounds according to 3) of composition C is in the range of 0.001% to 20% by weight, preferably in the range of 0.005% to 15% by weight, more preferably in the range of 0.01% to 12% by weight, still more preferably in the range of 0.03% to 10% by weight, calculated to the total weight of composition C.

<49> The product according to any of the clauses <1> to <48> characterized in that the total concentration of hydantoin and/or its salt(s) in composition C is in the range of 0.001% to 20% by weight, preferably in the range of 0.005% to 15% by weight, more preferably in the range of 0.01% to 12% by weight, still more preferably in the range of 0.03% to 10% by weight, calculated to the total weight of composition C.

<50> The product according to any of the clauses <1> to <49> characterized in that the total concentration of compounds according to groups 1) to 3) in composition C is in the range of 0.001% to 100% by weight, preferably in the range of 0.005% to 90% by weight, more preferably in the range of 0.01% to 80% by weight, still more preferably in the range of 0.03% to 75% by weight, calculated to the total weight of composition C.

<51> The product according to any of the clauses <1> to <49> characterized in that composition C is a powder composition comprising one or more pulverulent excipient.

<52> The product according to clause <51> characterized in that the pulverulent excipient of composition C is selected from diatomaceous earth, kaolin, bentonite, starch especially corn, tapioca, rice, wheat and potato, nylon powder, montmorillonit, gypsum, sawdust and perlite.

<53> The product according to any of the clauses <51> to <52> characterized in that the concentration of one or more pulverulent excipient in composition C is 10% by weight or more, more preferably 20% by weight or more, further more preferably 30% by weight or more, still more preferably 50% by weight or more, still more preferably 80% by weight or more, still more preferably 90% by weight or more, calculated to the total weight of the composition C.

<54> The product according to any of the clauses <1> to <49> characterized in that composition C is an aqueous composition.

<55> The product according to any of the clauses <1> to <49> and/or <54> characterized in that the total concentration of water in composition C is 10% by weight or more, more preferably 20% by weight or more, further more preferably 30% by weight or more, still more preferably 50% by weight or more, still more preferably 80% by weight or more, still more preferably 90% by weight or more, calculated to the total weight of composition C.

<56> The product according to any of the clauses <1> to <49> and/or <54> to <55> characterized in that compositions A, B, and/or C is/are thickened gel(s) and/or emulsion (s).

<57> The product according to any of the clauses <1> to <56> characterized in that compositions A, B, and/or C comprise one or more lipophilic compound(s).

<58> The product according to clause <57> characterized in that one or more lipophilic compound(s) is/are selected from $C_{12}$ to $C_{22}$ fatty alcohols, esters of $C_3$ to $C_{22}$ alcohols with $C_{12}$ to $C_{22}$ fatty acids, $C_8$ to $C_{22}$ fatty acids, vegetable oils, and/or silicones, and/or hydrocarbon-based products, and/or their mixtures.

<59> The product according to any of the clauses <57> and/or <58> characterized in that the total concentration of lipophilic compound(s) in compositions A, B, and/or C is in the range of 1% to 20% by weight, preferably in the range of 2% to 15% by weight, more preferably in the range of 3% to 12% by weight, calculated to the total weight of each of the compositions A, B, and/or C.

<60> The product according to any of the clauses <1> to <59> characterized in that compositions A, B, and/or C comprise one or more surfactant(s), preferably selected from non-ionic surfactants, anionic surfactants, cationic surfactants, and/or amphoteric/zwitterionic surfactants, and/or their mixtures, more preferably selected from anionic surfactants.

<61> The product according to clause <60> characterized in that the total concentration of one or more surfactant(s) in compositions A, B, and/or C is in the range of 0.1% to 10% by weight, calculated to the total weight of each of the compositions A, B, and/or C.

<62> The product according to any of the clauses <1> to <61> characterized in that compositions A, B, and/or C comprise(s) one or more thickening polymer.

<63> The product according to clause <62> characterized in that one or more thickening polymer(s) is/are selected from non-ionic thickening polymers and/or anionic thickening polymers, and/or their mixtures, and/or their salt(s).

<64> The product according to any of the clauses <62> to <63> characterized in that the total concentration of thickening polymers the compositions A, B, and/or C is in the range of 0.1% to 15% by weight, preferably in the range of 0.25% to 12% by weight, more preferably in the range of 0.5% to 10% by weight, calculated to the total weight of the compositions A, B, and/or C.

The present disclosure is also directed to <65> a method for dyeing of keratin fibers, preferably human keratin fibers, more preferably human hair, comprising the steps of:
  i) providing compositions A, B, and C as defined in any of the clauses <1> to <8> and/or <11> to <64>,
  ii) mixing the compositions to yield a ready-to-use composition having a pH in the range of 7 to 12,
  iii) applying the ready-to-use composition onto keratin fibers
  iv) leaving it for a time period of 1 to 60 min and optionally heating the keratin fibers to a temperature range in the range of 40° C. to 60° C.
  v) rinsing off the keratin fibers and optionally shampooing the keratin fibers.

<66> The method according to clause <65> characterized in that the ready-to-use composition of steps ii) and iii) has a pH in the range of 7 to 12, preferably in the range of 7.5 to 11, more preferably in the range of 8.0 to 10.5.

<67> The method according to any of the clauses <65> to <66> characterized in that ready-to-use composition in step iv) is left onto keratin fibers for a time period of 1 min to 60 min, preferably for a time period of 5 min to 45 min, more preferably for a time period of 10 min to 35 min.

<68> The method according to any of the clauses <66> to <67> characterized in that during the application time of the ready-to-use mixture in step iv), heat may be applied to the keratin fibers, preferably in a temperature range from 30° C. to 50° C.

The present disclosure is also directed to <69> a method for bleaching and/or dyeing of keratin fibers, preferably human keratin fibers, more preferably human hair, comprising the steps of:
  xi) providing compositions A, B, and C as defined in any of the clauses <1> to <64>,
  xii) mixing the compositions to yield a ready-to-use composition having a pH in the range of 7 to 12,
  xiii) applying the ready-to-use composition onto keratin fibers
  xiv) leaving it for a time period of 1 to 60 min and optionally heating the keratin fibers to a temperature range in the range of 40° C. to 60° C.

xv) rinsing off the keratin fibers and optionally shampooing the keratin fibers.

<70> The method according to clause <69> characterized in that the ready-to-use composition of steps xii) and xiii) has a pH in the range of 7 to 12, preferably in the range of 7.5 to 11, more preferably in the range of 8.0 to 10.5.

<71> The method according to any of the clauses <69> to <70> characterized in that ready-to-use composition in step xiv) is left onto keratin fibers for a time period of 1 min to 60 min, preferably for a time period of 5 min to 45 min, more preferably for a time period of 10 min to 35 min.

<72> The method according to any of the clauses <69> to <71> characterized in that during the application time of the ready-to-use mixture in step xiv), heat may be applied to the keratin fibers, preferably in a temperature range from 30° C. to 50° C.

The following examples are to illustrate the invention, but not to limit it.

EXAMPLES

Example 1

|  | % by weight |
|---|---|
| Composition A |  |
| Hydroxyethylcellulose | 3 |
| Tetrasodium EDTA | 2 |
| Sodium carbonate | 1 |
| Ammonium persulfate | 11 |
| Potassium persulfate | 36 |
| Sodium metasilicate | 10 |
| Mineral oil | 8 |
| Diatomaceous Earth | to 100 |
| Composition B |  |
| Cetearyl alcohol | 4.0 |
| Sodium lauryl sulfate | 0.8 |
| Phosphoric acid | q.s. ad pH 1.5 |
| Tetrasodium EDTA | 0.05 |
| Hydrogen peroxide | 6.0 |
| Water | ad 100.0 |
| Composition C |  |
| Caffeine | 100 |

Compositions A and B were mixed in a weight ratio 1:1.4 and composition C was added (yielding 0.004% to 0.4% by weight of caffeine in ready-to-use mixture).

The following damage reduction values were revealed, while maintaining the same degree of lightening:

|  | Comp. ex | Inv. Ex. 1 | Inv. Ex. 2 | Inv. Ex. 3 | Inv. Ex. 4 |
|---|---|---|---|---|---|
|  |  | [% by weight] | | | |
| Caffeine conc. in ready-to-use mixture | 0 | 0.004 | 0.02 | 0.08 | 0.4 |
| Damage reduction [%] | — | 8.0 | 8.0 | 6.0 | 6.0 |

The following compositions C were prepared:

| Ingredients | Inv. ex. 5 | Inv. ex. 6 | Inv. ex. 7 | Inv. ex. 8 | Inv. ex. 9 | Inv. ex. 10 | Inv. ex. 11 | Inv. ex. 12 | Inv. ex. 13 | Inv. ex. 14 | Inv ex. 15 |
|---|---|---|---|---|---|---|---|---|---|---|---|
| Caffeine | 50.0 | 10.0 | — | — | — | — | — | — | — | — | — |
| Tiron | — | — | 50.0 | 10.0 | — | — | — | 0.5 | — | — | — |
| Hydantoin | — | — | — | — | 50.0 | 10.0 | — | — | — | — | — |
| Allantoin | — | — | — | — | — | — | 50.0 | — | — | — | — |
| Gallic acid | — | — | — | — | — | — | — | — | 50.0 | 10.0 | — |
| 4-methyl catechol | — | — | — | — | — | — | 0.05 | — | — | 50.0 | 10.0 |
| Diatomaceous earth | Ad 100.0 | — | Ad 100.0 | — | Ad 100.0 | — | Ad 100.0 | Ad 100.0 | — | Ad 100.0 | — |
| Water | — | Ad 100.0 | — | Ad 100.0 | — | Ad 100.0 | — | — | Ad 100.0 | — | Ad 100.0 |
| % by weight in ready-to-use comp. | 0.4 | 0.08 | 0.4 | 0.08 | 0.4 | 0.08 | 0.404 | 0.404 | 0.08 | 0.4 | 0.08 |
| Damage reduction [%] | 5.6 | 8.4 | 9.1 | 16.2 | 11.6 | 16.2 | 8.4 | 4.0 | 1.6 | 8.6 | 4.5 |

Compositions A and B were mixed in a weight ratio 1:1.4 and composition C was added (yielding 0.08% to 0.404% by weight of caffeine in ready-to-use mixture).

Methods

Hair Bleaching

To human hairstreaks (21 cm, 2 g per bundle) were applied 12.1 g of the ready-to-use compositions mixed as explained above and left for 30 min at 40° C. The hairstreaks were then rinsed-off with lukewarm water, shampooed with a shampoo commercially available under the trade name Goldwell Deep Cleansing Shampoo, and blow-dried. The color was measured as outlined below.

Hair Damage Assessment

For damage assessment 25 hairs of each sample were measured with a Diastron Tensile tester under wet conditions to achieve stress-strain curves. Since the post-yield region can be attributed to the influence of the sulfur bonds, which are weakened due to oxidation during the bleaching process, this was seen as indicator for the oxidative damage. The post-yield gradient was calculated and compared to the post-yield gradient gained using the same bleach mixture, but without the active agent from composition C.

The following examples are within the scope of the present invention.

Example 16

| | % by weight |
|---|---|
| Composition A | |
| Hydroxyethylcellulose | 3 |
| Tetrasodium EDTA | 2 |
| Sodium carbonate | 1 |
| Ammonium persulfate | 11 |
| Potassium persulfate | 36 |
| Sodium metasilicate | 10 |
| HC Blue 18 | 0.2 |
| HC Red 18 | 0.05 |
| HC Yellow 16 | 0.01 |
| Mineral oil | 8 |
| Diatomaceous Earth | to 100 |
| Composition B | |
| Cetearyl alcohol | 4.0 |
| Sodium lauryl sulfate | 0.8 |
| Phosphoric acid | q.s. ad pH 2.5 |
| Hydrogen peroxide | 9.0 |
| Water | ad 100.0 |
| Composition C | |
| Tiron disodium salt | 0.05 |
| Water | ad 100.0 |

Example 17

| | % by weight |
|---|---|
| Composition A | |
| Aminomethyl propanol | 5.0 |
| HC Red 18 | 0.4 |
| HC Yellow 16 | 0.1 |
| HC Blue 18 | 1.0 |
| Fragrance | q.s. |
| Diatomaceous Earth | to 100 |

| | % by weight |
|---|---|
| Composition B | |
| Cetearyl alcohol | 4.0 |
| Sodium lauryl sulfate | 0.8 |
| Phosphoric acid | q.s. ad pH 2.5 |
| Hydrogen peroxide | 9.0 |
| Water | ad 100.0 |
| Composition C | |
| Hydantoin | 0.05 |
| Water | ad 100.0 |

The invention claimed is:

1. A cosmetic product, comprising:
   a composition A comprising one or more alkalizing agents;
   an aqueous composition B having a pH in a range of 1 to 6 and comprising one or more oxidizing agents; and
   a composition C comprising one or more compounds selected from the following groups:
   1)

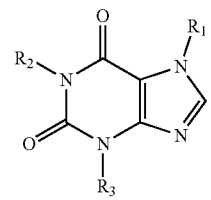

wherein $R_1$, $R_2$, and $R_3$ are independently selected from H and $CH_3$,
   2) one or more orthodiphenols and salts thereof, and
   3) one or more imidazolidin-2,4-diones and salts thereof, and
   wherein a concentration of any of the compounds according to groups 1) to 3) in composition C is in the range of 50% to 100% by weight, calculated to the total weight of composition C.

2. The cosmetic product according to claim 1, wherein the composition A is a bleaching powder composition comprising one or more bleaching agents selected from persalts and peroxy salts.

3. The cosmetic product according to claim 1, wherein the composition A is an aqueous composition having a pH in a range of 8 to 12.

4. The cosmetic product according to claim 1, wherein the composition A is a dyeing composition comprising one or more oxidative dye couplers, oxidative dye precursors, or comprising one or more non-ionic, anionic, cationic, and/or amphoteric dyes.

5. The cosmetic product according to claim 1, wherein the composition A further comprises one or more direct dyes selected from Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, DC Violet 2, DC Red 33, DC Orange 4, DC Red 27, DC Yellow 10, HC Blue 18, HC Red 18, and HC Yellow 16, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12, Basic Red 22, Basic Red 76, Basic Violet 1, Basic Violet 2, Basic Violet 3, Basic Violet 10, Basic Violet 14, Basic Yellow 57, Basic Red 51, Basic Yellow 87, HC Blue 17, Basic Orange 31, Basic Blue 124, HC Blue No.2, HC Blue No.4, HC Blue No.5, HC Blue No.6, HC Blue No.7, HC Blue No.8, HC Blue No.9, HC Blue No. 10, HC Blue No. 11, HC Blue No. 12, HC Blue No. 13, HC Brown No.1, HC Brown No.2, HC Green No. 1, HC Orange No.1, HC Orange No.2, HC Orange No.3, HC Orange No.5, HC Red BN, HC Red No.1, HC Red No.3, HC Red No.7, HC Red No.8, HC Red No.9, HC Red No.10, HC Red No.11, HC Red No. 13, HC Red No.54, HC Red No. 14, HC Violet BS, HC Violet No. 1, HC Violet No.2, HC Yellow No.2, HC Yellow No.4, HC Yellow No. 5, HC Yellow No.6, HC Yellow No.7, HC Yellow No.8, HC Yellow No.9, HC Yellow No.10, HC Yellow No.11, HC Yellow No. 12, HC Yellow No.13, HC Yellow No. 14, HC Yellow No. 15, 2-amino-6-chloro-4-nitrophenol, tetrabromophenol blue, picramic acid, 2-hydroxyethylpicramic acid, and salts thereof.

6. The cosmetic product according to claim 5, wherein the one or more direct dyes in the composition A are selected from HC Blue 18, HC Red 18, HC Yellow 16, Disperse Black 9, Acid Yellow 1, 2-amino-6-chloro-4-nitrophenol, tetrabromophenol blue, and salts thereof.

7. The cosmetic product according to claim 5, wherein a total concentration of the one or more direct dyes in the composition A is in a range of 0.001% to 10% by weight, calculated to the total weight of the composition A.

8. The cosmetic product according to claim 1, wherein the one or more compounds according to group 1) of the composition C are caffeine or theobromine.

9. The cosmetic product according to claim 1, wherein the one or more compounds according to group 2) in the composition C are selected from Flavonols, Anthocyanidines, Anthocyanines, anthocyanes, Orthohydroxybenzoates, Flavones, Hydroxystilbenes, 3,4-dihydroxyphenylalanine and its derivatives, 2,3-dihydroxyphenylalanine and its derivatives, 4,5-dihydroxyphenylalanine and its derivatives, Dihydroxycinnamates, Orthopolyhydroxycoumarines, Orhtopolyhydroxyisocoumarines, Orthopolyhydroxycoumarones, Orthopolyhydroxyisocoumarones, Orhtopolyhydroxychalcones, Orhtopolyhydroxychromones, Orhtopolyhydroxyquinones, Orhtohydroxyxanthones, 1,2-dihydroxybenzenes and its derivatives, 1,2,4-trihydroxy benzenes and its derivatives, 1,2,3-trihydroxybenzenes and its derivatives, 2,4,5-trihydroxybenzenes and its derivatives, Proanthocyanidines, Proanthocyanines, Tannic acid, Ellagic acid, and one or more compounds according the following general structure:

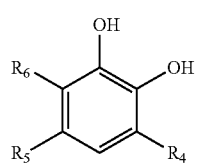

wherein $R_4$, $R_5$, and $R_6$ are independently selected from H, OH, halogen, $C_1$-$C_{12}$ linear or branched alkyl or alkenyl, O—X, $NO_2$, COOH, $SO_3H$, aryl, heteroaryl, and salts thereof, and X is a $C_1$-$C_{12}$ linear or branched alkyl.

10. The cosmetic product according to claim 1, wherein the one or more compounds according to group 2) in the composition C are selected from the following general structure:

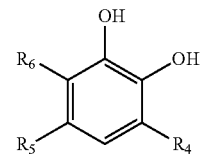

wherein $R_4$, $R_5$, and $R_6$ are independently selected from H, OH, halogen $C_1$-$C_{12}$ linear or branched alkyl or alkenyl, O—X, $NO_2$, COOH, $SO_3H$, aryl, heteroaryl, and salts thereof, and X is a $C_1$-$C_{12}$ linear or branched alkyl.

11. The cosmetic product according to claim 1, wherein the one or more compounds according to group 2) of the composition C is selected from:

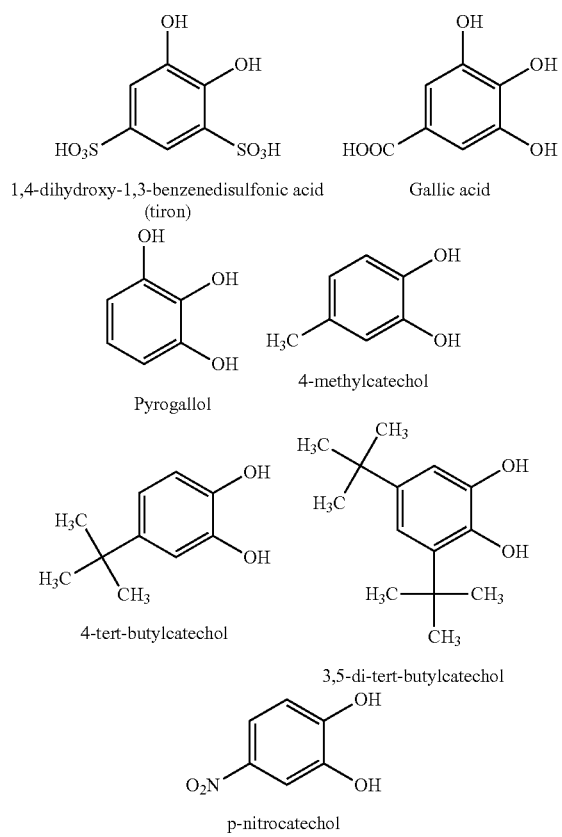

and salts thereof.

12. The cosmetic product according to claim 1, wherein the one or more compounds according to group 3) of the composition C is according to the following general structure:

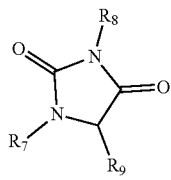

wherein $R_7$, $R_8$, and $R_9$ are independently selected from H, OH, halogen, $C_1$-$C_{12}$ linear or branched alkyl or alkenyl, O—X, COOH, phenyl, diphenyl, ureyl, and salts thereof and X is a $C_1$-$C_{12}$ linear or branched alkyl.

13. The cosmetic product according to claim 1, wherein the composition C is a powder composition comprising one or more pulverulent excipients selected from diatomaceous earth, kaolin, bentonite, starch, tapioca, rice, wheat, potato, nylon powder, montmorillonite, gypsum, sawdust and perlite.

14. The cosmetic product according to claim 1, wherein the composition C is an aqueous composition, and a total concentration of water in the composition C is 10% by weight or more, calculated to the total weight of composition C.

15. A method for bleaching and/or dyeing of keratin fibers, comprising:
mixing the composition A, the aqueous composition B, and the composition C of claim 1 to yield a ready-to-use composition having a pH in a range of 7 to 12;
applying the ready-to-use composition onto the keratin fibers;
leaving it for a time period of 1 to 60 min and optionally heating the keratin fibers to a temperature in a range of 40° C. to 60° C.; and
rinsing off the keratin fibers and optionally shampooing the keratin fibers.

16. The cosmetic product according to claim 1, wherein the one or more compounds according to group 1) of the composition C is caffeine.

17. The cosmetic product according to claim 1, wherein the one or more compounds according to group 2) in the composition C are selected from the following general structure:

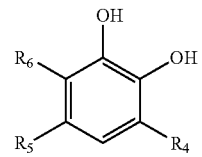

wherein $R_4$ is selected from H, OH, halogen $C_1$-$C_{12}$ linear or branched alkyl or alkenyl, O—X, $NO_2$, COOH, $SO_3H$, aryl, heteroaryl, $R_5$ and $R_6$ are independently selected from $C_1$-$C_{12}$ linear or branched alkyl or alkenyl, O—X, $NO_2$, COOH, $SO_3H$, and salts thereof, and X is a $C_1$-$C_{12}$ linear or branched alkyl.

18. The cosmetic product according to claim 1, wherein the one or more compounds according to group 2) of the composition C are selected from tiron, gallic acid, 4-methylcatechol, and salts thereof.

19. The cosmetic product according to claim 1, wherein the one or more compounds according to group 3) of the composition C are selected from hydantoin, allantoin, and salts thereof.

20. A cosmetic product comprising:
a composition A comprising one or more alkalizing agents;
an aqueous composition B having a pH in the range of 1 to 6 and comprising one or more oxidizing agents; and
a composition C comprising one or more compounds selected from the following groups:
1)

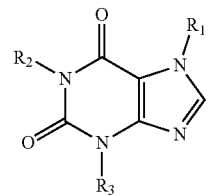

wherein $R_1$, $R_2$, and $R_3$ are independently selected from H and $CH_3$,
2) one or more orthodiphenols and salts thereof, and
3) one or more imidazolidin-2,4-diones and salts thereof, and
wherein the composition C is anhydrous.

* * * * *